United States Patent
Aarts et al.

(10) Patent No.: US 9,132,333 B2
(45) Date of Patent: Sep. 15, 2015

(54) METHOD AND SYSTEM FOR MAINTAINING A STATE IN A SUBJECT

(75) Inventors: Ronaldus Maria Aarts, Eindhoven (NL); Mark Thomas Johnson, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 428 days.

(21) Appl. No.: 12/993,861

(22) PCT Filed: May 29, 2009

(86) PCT No.: PCT/IB2009/052271
§ 371 (c)(1),
(2), (4) Date: Nov. 22, 2010

(87) PCT Pub. No.: WO2009/147599
PCT Pub. Date: Dec. 10, 2009

(65) Prior Publication Data
US 2011/0082511 A1    Apr. 7, 2011

(30) Foreign Application Priority Data
Jun. 6, 2008 (EP) .................................. 08157701

(51) Int. Cl.
*A61N 1/00* (2006.01)
*A63B 71/06* (2006.01)
(Continued)

(52) U.S. Cl.
CPC ......... *A63B 71/0686* (2013.01); *A61B 5/02405* (2013.01); *A61B 5/486* (2013.01);
(Continued)

(58) Field of Classification Search
CPC ............. A61N 1/36078; A61N 1/3611; A61B 5/02405; A61B 5/486; A61B 5/0482
USPC .............................................. 607/11; 600/513
See application file for complete search history.

(56) References Cited

U.S. PATENT DOCUMENTS

| 4,800,893 A * | 1/1989 | Ross et al. .................... 600/545 |
| 5,800,337 A | 9/1998 | Gavish |
| 6,212,427 B1 | 4/2001 | Hoover |
| 6,305,943 B1 | 10/2001 | Pougatchev et al. |
| 6,493,578 B1 * | 12/2002 | DeFeo .......................... 600/546 |
| 6,902,296 B2 * | 6/2005 | Searfoss, III ................. 362/231 |

(Continued)

FOREIGN PATENT DOCUMENTS

| JP | 2004222818 A | 8/2004 |
| WO | 2005044092 A2 | 5/2005 |
| WO | 2007093988 A2 | 8/2007 |

OTHER PUBLICATIONS

Patterson et al: "Voluntary Cardio-Respiratory Synchronization"; IEEE Engineering in Medicine and Biology Magazine, Nov./Dec. 2004, vol. 23, No. 6, pp. 52-56.

*Primary Examiner* — Niketa Patel
*Assistant Examiner* — William Levicky

(57) ABSTRACT

A method of maintaining a state in a subject (12) comprises generating a pacing signal (20) at a first frequency, presenting to the subject an output based upon the generated pacing signal, measuring one or more physiological parameters of the subject, detecting that the measured parameter(s) conform to a desired state in the subject, and either removing the presentation to the subject of the output based upon the generated pacing signal, or generating a new pacing signal at a second frequency, and presenting to the subject an output based upon the generated new pacing signal. The method can further comprise, prior to the detecting that the measured parameter(s) conform to a desired state in the subject, adjusting the pacing signal according to feedback from the measured parameter(s). In a preferred embodiment, the method also further comprises detecting that the measured parameter(s) no longer conform to a desired state in the subject, and presenting to the subject an output based upon the original generated pacing signal.

8 Claims, 5 Drawing Sheets

(51) Int. Cl.
*A61N 1/36* (2006.01)
*A61B 5/024* (2006.01)
*A61B 5/00* (2006.01)
*A63B 23/18* (2006.01)
*A63B 24/00* (2006.01)

(52) U.S. Cl.
CPC ......... *A61N 1/3611* (2013.01); *A61N 1/36078* (2013.01); *A63B 23/185* (2013.01); *A63B 24/0075* (2013.01); *A63B 2071/0625* (2013.01); *A63B 2220/807* (2013.01); *A63B 2230/06* (2013.01); *A63B 2230/062* (2013.01); *A63B 2230/50* (2013.01)

(56) References Cited

U.S. PATENT DOCUMENTS

| | | | |
|---|---|---|---|
| 8,543,197 B2* | 9/2013 | Striepe et al. | 600/513 |
| 2004/0077934 A1* | 4/2004 | Massad | 600/300 |
| 2004/0077975 A1* | 4/2004 | Zimmerman | 600/595 |
| 2005/0113707 A1* | 5/2005 | Stabler et al. | 600/523 |
| 2005/0187426 A1 | 8/2005 | Elliott | |
| 2005/0288601 A1 | 12/2005 | Wood et al. | |
| 2006/0047202 A1 | 3/2006 | Elliott | |
| 2006/0064037 A1* | 3/2006 | Shalon et al. | 600/586 |
| 2007/0299354 A1 | 12/2007 | Striepe et al. | |
| 2009/0124920 A1* | 5/2009 | Patterson et al. | 600/544 |
| 2011/0060235 A1* | 3/2011 | Crompvoets et al. | 600/509 |

* cited by examiner

METHOD AND SYSTEM FOR MAINTAINING A STATE IN A SUBJECT

FIELD OF THE INVENTION

This invention relates to a method and system for maintaining a state in a subject. In one embodiment, the invention can be used to deliver a system using flexible and optimal breathing guidance algorithms.

BACKGROUND OF THE INVENTION

In recent years heart-rate variability has become a topic of major interest, both in physiology and in psychology. One reason for the interest is that heart-rate variability is attributed to the balance between the parasympathetic and the sympathetic nervous system, respectively decreasing and increasing the heart rate. Beyond clinical interest there are known applications for use with a subject, including decreasing the sleep-onset time, yoga exercises, lowering the blood pressure, relaxation during computer use or television watching, vehicle driving, medicine, and sports situations.

The connection between being relaxed via meditation and breathing is shown in studies on the impact of meditation on cardio-respiratory synchronization with respect to breathing oscillations and the modulations of heart rate induced by respiration, known as respiratory sinus arrhythmia (RSA). Zen meditation synchronizes the cardio-respiratory interaction with respect to breathing oscillations and the heart rate variations induced by respiration. Furthermore, such meditation also drastically increases low-frequency variations of heart rate. Spontaneous breathing patterns hardly showed any cardio-respiratory synchronization and during mental activity the cardio-respiratory synchronization was decreased compared to both types of Zen meditation. It may also be shown that this kind of cardio-respiratory synchronization is advantageous for the gas exchange in the respiratory tract. Furthermore, it is known that this kind of religious practice has immediate physiological effects on cardio-respiratory interaction without the need of special long-term training. For yoga similar results are obtained.

Before 1964, the only method to control the respiratory induced variation was for the subject or patient to hold his breath. In 1964, the first known solution to the respiratory variations in the electrocardiogram/vector cardiogram (ECG/VCG) was in a paper Otto Schmitt published on techniques for signal averaging. In this paper, subjects were signalled using a light or sound to breathe, synchronized at a sub multiple of their heart rate. The signal was created from the ECG by counting, for example, two beats for the inspiration signal and the next three beats for the expiration signal. Each of the beats or time intervals with the same position in the respiratory cycle (i.e., first, second, third, etc.) were computer averaged to eliminate noise and other variations that occur unsynchronized with the heart beat. This resulted in a very noise-free signal representing respiratory sinus arrhythmia (RSA) changes in the beat-to-beat heart rate or RR interval. The non-respiration variations are reduced as the square root of number of breath cycles.

According to one aspect of the invention, a primary station comprises an array A current product is RESPeRATE®, which is a portable electronic device that helps lower blood pressure naturally by device-guided breathing. The device uses the body's natural tendency to follow external rhythms, interactively guiding the subject to reduce their breathing rate to a "therapeutic zone" of fewer than ten breaths per minute. This is the only medical device clinically proven to lower blood pressure through paced breathing therapy and is available for sale without a prescription.

A more complex system is disclosed in United States of America Patent Application Publication US 2005/0187426, which discloses a system and method for synchronizing the heart rate variability cycle with the breathing cycle. This publication describes a method and system for achieving coherence of heart rate variability by synchronizing the heart rate variability cycle to the breathing cycle and by consciously synchronizing the breathing cycle with an external reference that is closely aligned with the frequency of the natural heart rate variability cycle. Various means of representing the cycle of the external reference are provided including visual, audible, and sensory indicators. An instructive method is provided that teaches the subject to consciously synchronize their inhalation with the positive going aspect of the external reference cycle and their exhalation with the negative going aspect of the external reference cycle.

All of the presently known systems lack sufficient flexibility in the guidance system presented to the subject.

SUMMARY OF THE INVENTION

It is therefore an object of the invention to improve upon the known art.

According to a first aspect of the present invention, there is provided a method of maintaining a state in a subject comprising generating a pacing signal at a first frequency, presenting to the subject an output based upon the generated pacing signal, measuring one or more physiological parameters of the subject, detecting that the measured parameter(s) conform to a desired state in the subject, and either removing the presentation to the subject of the output based upon the generated pacing signal, or generating a new pacing signal at a second frequency, and presenting to the subject an output based upon the generated new pacing signal.

According to a second aspect of the present invention, there is provided a system for maintaining a state in a subject comprising a processor arranged to generate a pacing signal at a first frequency, one or more output devices arranged to present to the subject an output based upon the generated pacing signal, and one or more sensors arranged to measure one or more physiological parameters of the subject, wherein the processor is further arranged to detect that the measured parameter(s) conform to a desired state in the subject, and either to remove the presentation to the subject of the output based upon the generated pacing signal, or to generate a new pacing signal at a second frequency, the output device(s) arranged to present to the subject an output based upon the generated new pacing signal.

Owing to the invention, it is possible to provide a method and system for maintaining a state in the subject that will provide feedback to the subject that is more flexible than in presently known systems. Once the user has obtained the desired state, as determined by the measurement of their physiological parameters, then the actual feedback to the user will either by removed or changed to reflect their current state. This provides a system that is more attuned to the real need of the subject, which is likely to change, once they have entered the desired state.

Advantageously, the method further comprises, prior to the detecting that the measured parameter(s) conform to a desired state in the subject, adjusting the pacing signal according to feedback from the measured parameter(s). While the subject is in an initial state, before the desired state is reached, then the physiological parameter(s) can be measured to determine the subject's respiratory sinus arrhythmia, and small changes to the pacing signal can be made to assist the user in attaining the desired state.

Preferably, the method further comprises detecting that the measured parameter(s) no longer conform to a desired state in the subject, and presenting to the subject an output based upon the original generated pacing signal. After the subject has reached the desired state, then either the output is removed or changed. However, the subject can still be monitored, and if they are detected to have moved from the desired state, then the system can adapt to bring back an output based upon the original pacing signal, in order to once again return the subject to the desired state. Additionally, or alternatively, the method could further comprise, in this situation of detecting that the measured parameter(s) no longer conform to a desired state in the subject, presenting to the subject a warning indication. The warning tells the subject that they are no longer in the desired state, and the subject can decide whether to restart the process or take some other action.

Ideally, the method further comprises, following detecting that the measured parameter(s) conform to a desired state in the subject, and prior to either removing the presentation to the subject of the output based upon the generated pacing signal, or generating a new pacing signal at a second frequency, and presenting to the subject an output based upon the generated new pacing signal, maintaining the desired state in the subject for a predetermined length of time. The change in the output to the subject, by removing or altering the output, need not occur directly after it is detected that the subject has entered the desired state. A time lapse could be included in the system, before the change is instigated.

BRIEF DESCRIPTION OF THE DRAWINGS

Embodiments of the present invention will now be described, by way of example only, with reference to the accompanying drawings, in which.

DETAILED DESCRIPTION OF THE EMBODIMENTS

Figure 1:
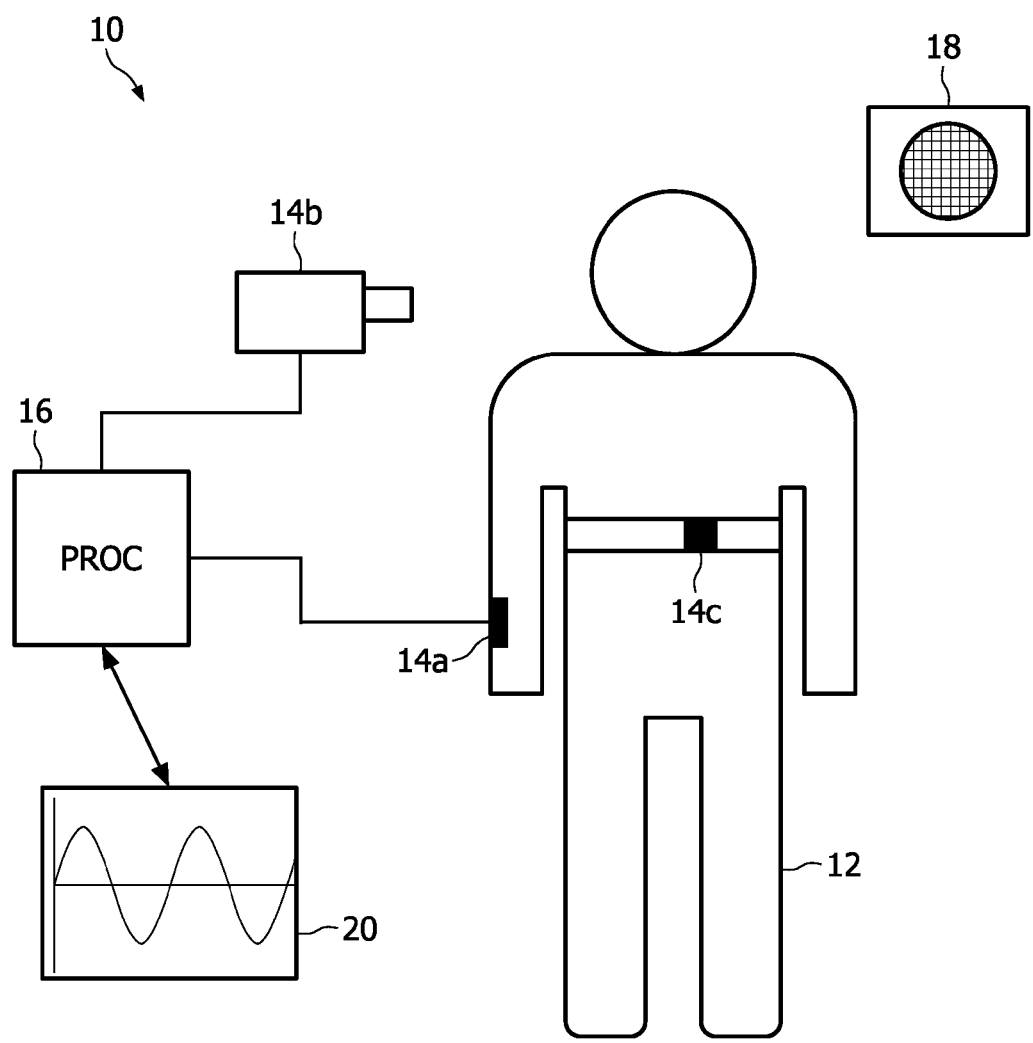
FIG. 1 is a schematic diagram of a system with a subject.

FIG. 1 shows a system 10 for maintaining a state in a subject 12. The system 10 comprises sensors 14 which are arranged to measure one or more physiological parameters of the subject 12, a processor 16 arranged to perform various calculations using the measured parameter(s), and an output device 18 arranged to generate an output to the subject 12. The system 10 is effectively a feedback system, monitoring the parameters of the subject 12, such as skin temperature and heart rate, and providing feedback to the subject 12 via the output device 18. The processor 16 generates a pacing signal 20, and the subject 12 is presented with an output based upon the generated pacing signal 20.

The Figure shows the subject 12 being monitored by three separate sensors 14. The sensor 14a is skin conductivity measuring device, the sensor 14b is a camera that is monitoring the facial expression and head position of the subject 12, and the sensor 14c is a wireless heart rate monitor held in place with a strap around the subject's chest. The sensors 14a and 14c can be considered to be direct sensors that are directly measuring physiological parameters of the subject 12, and the sensor 14b is an indirect sensor that is measuring physiological parameters such as the facial expression of the subject 12. Other indirect physiological sensors may comprise the manner in which user interacts with a user interface, for example the pressure at which the user grips a steering wheel.

The output device 18 is a loudspeaker arranged to provide an output to the subject 12, under the control of the processor 16. A single output device 18 is shown in the Figure, but there is no reason why multiple output devices 18 can be used, of the same or of a different category. For example, an output device 18 may be provided that constitutes a display device. The subject 12 is provided with a feedback via the audio device 18 and also, in concert, by the associated display device. The output devices 18, or a single output device 18, go to providing the totality of the feedback to the subject 12, under the control of the processor 16, which determines the extent and pace of the feedback provided to the subject 12, by the device(s) 18.

In one embodiment, the system 10 of FIG. 1 can be used to provide help to the subject 12 with respect to their breathing. Breathing guidance are methods to improve the subject's breathing techniques. Breathing influences heart rate and hence heart-rate variability. This is of particular interest because heart-rate variability is attributed to the balance between the parasympathetic and the sympathetic nervous system, respectively decreasing and increasing the subject's heart rate. In this preferred embodiment, the system 10 focuses in particular on the transition from voluntary cardio-respiratory synchronization (VCRS) to non-VCRS breathing and visa versa, and in optimizing the respiratory sinus arrhythmia (RSA) of the subject 12. The system 10 uses VCRS to give feedback to the subject 12 in a convenient, flexible, and general way in various applications, in particular sleep-onset and sports, but may be extended to other fields like relaxation in general and lowering the blood pressure of the subject 12 in particular.

Figure 2:
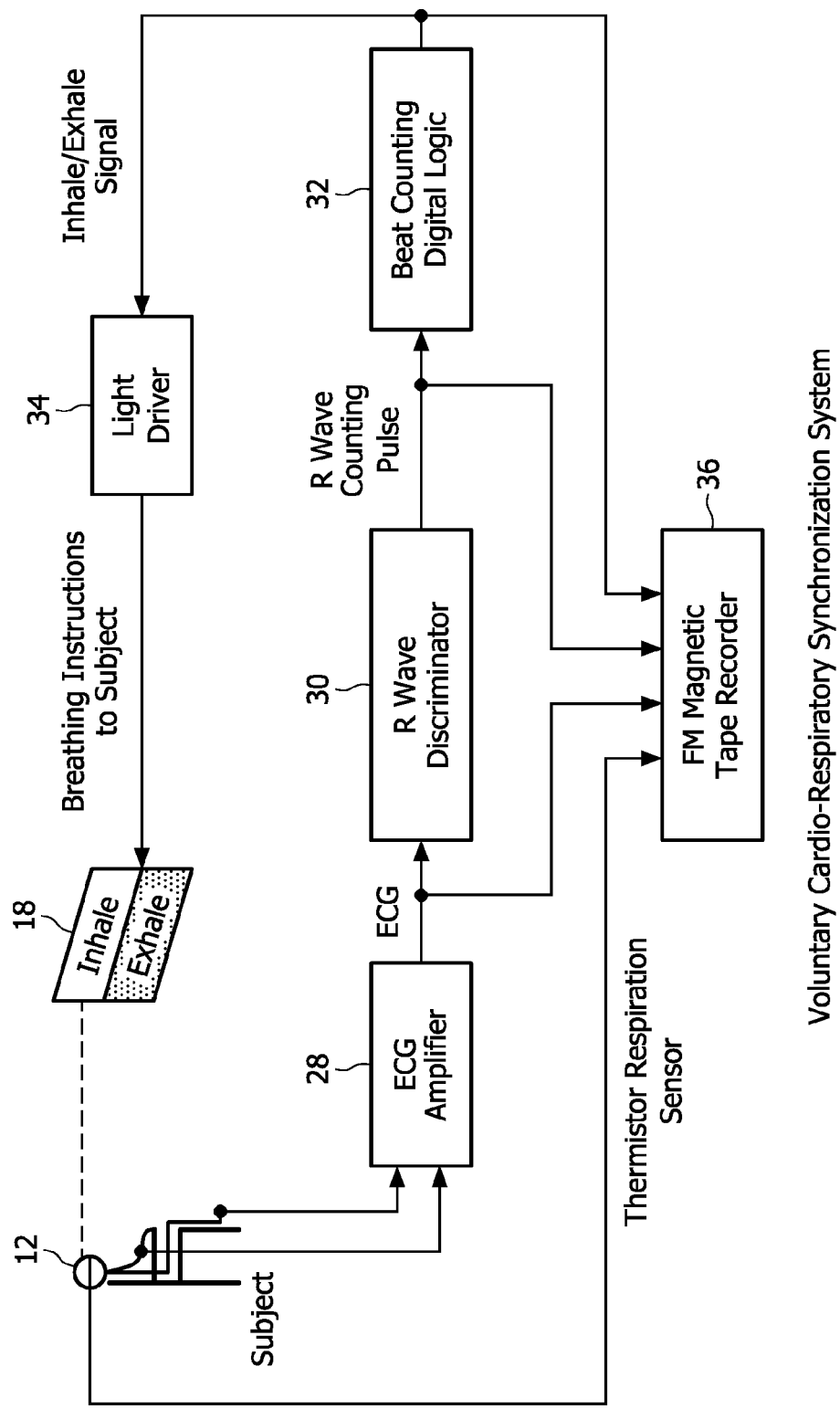
FIG. 2 is a schematic diagram of a voluntary cardio-respiratory synchronisation system.

FIG. 2 shows an example of a voluntary cardio-respiratory synchronisation (VCRS) scheme, which can be used to support a breathing level in a subject 12, in order to regulate the heart rate of the subject 12. The system of FIG. 2 can be used to maintain the heart rate (or the interpreted relaxation level) of the subject 12 within a desired state. The subject 12 is monitored and has the physiological parameters associated with their heart measured by sensors (not shown), the output of which is received at an ECG amplifier 28.

The amplified ECG signal is passed to an R wave discriminator 30, which outputs an R wave counting pulse to a beat counting logic circuit 32. This logic controls a light driver 34 which controls an output device 18, which is comprised of lights that illustrate to the subject 12 when the subject 12 should inhale and exhale. The system shown in FIG. 2 need not be intrusive for the subject 12, for example if they are wearing a small wrist-mounted device that monitors their heart rate. Output is provided to the subject 12, via the lights 18, based upon the pacing signal 20. The pacing signal 20 is used to provide feedback to the subject 12, in order to deliver breathing guidance to the subject 12. While the subject 12 is monitored by the system, then data can recorded at the recorder 36.

Figure 3:
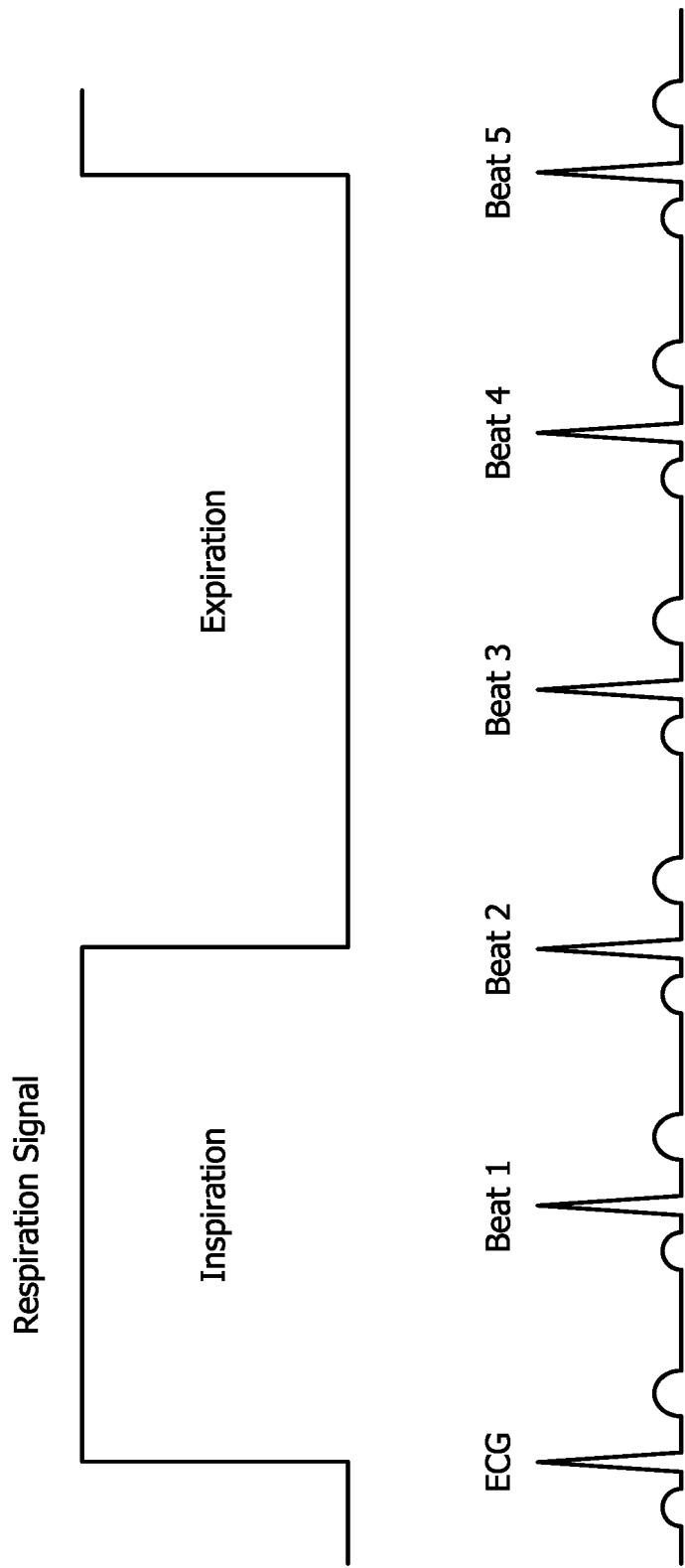
FIGS. 3 and 4 are timing diagrams.

FIG. 3 shows a VCRS timing diagram, with the output of the R wave discriminator 30 shown in the lower portion of the Figure, and the generation of a respiration signal at the top of the Figure. This respiration signal is used to control the lights 18, which signal to the subject 12 the information that the subject 12 needs in order to control their breathing. The scheme of FIGS. 2 and 3 is one way in which an output can be provided to a subject 12 in order to control, for example the relaxation level, of the subject 12. The breathing guidance delivered by the output of the system 10 can be utilised to allow the subject 12 to control their own breathing and this will lead to reduced heart-rate variability, which assists the subject 12 in being relaxed.

Figure 4:
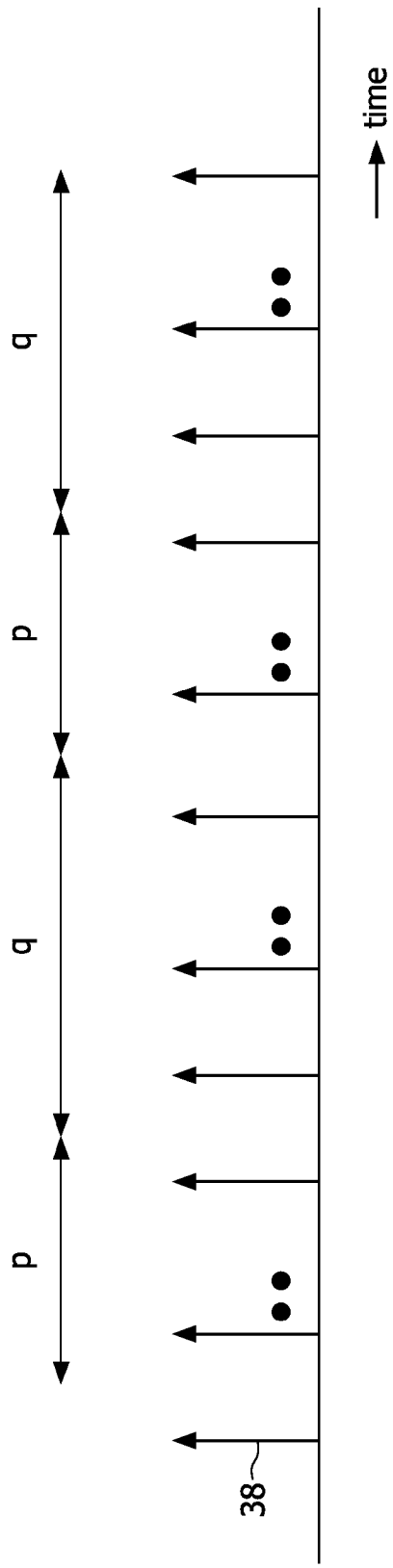

The system 10 contains three blocks, measuring (sensing), controlling, and feedback. The first step is the heart rate sensing which can be determined in a variety of ways. Preferably this measurement is unobtrusive and the preferred sensing method depends on the application. Once the ECG or a similar signal is known, the time between the R peaks can be determined, yielding the interbeat intervals (IBI). FIG. 4 shows a second timing diagram. The arrows 38 indicate a heartbeat of the subject 12, similar to the timing diagram of FIG. 3, but now the transients between intervals p and q and vice versa are not necessarily coincident with a subject's heart beat.

Looking at FIG. 4, the system 10 can assign intervals with real numbers p and q such that during the p interval or at the transition from q to p there is a "breath in" output signal to the subject 12, and at the transition from p to q there is a "breath out" output signal. Between the p and q intervals there are int(p) and int (q) heartbeats respectively, where 'int' denotes the integer operation. Heart beat is here considered in a wide sense; it can be derived directly from the ECG, but also from acoustics or the PPG. Note that p and q are not restricted to integers such as in ordinary VCRS, which gives more freedom to the subject 12, providing more freedom than systems which dictate that int(p)=int(q). The values of p and q may be chosen individually or even adapted to the subject 12, since this depends on the subject's tidal volume and cardiac output. The system 10 can even give feedback to the user 12 if the breathing is done properly as dictated by monitoring the respiration using PPG, or other means.

The transients between p and q and vice versa are not necessarily coincident with a heart beat. This gives important freedom; furthermore it makes more sense from a physiological point of view. In particular if the beat arrows 38 are derived from a finger PPG then there is a significant delay between the relevant pulse in the ECG and the PPG. The only restriction is that the intervals p and q vary proportional to the corresponding heart beat activity time axis, hence remaining phase locked. In the simplest embodiment p and q are integers, and thus coinciding with the measured pulse (the arrows 38 in FIG. 4).

In a more refined embodiment, the positions of the arrows 38 are predicted with an Auto Regressive (AR) filter, so that in cases that the measured signal is unreliable, the AR function predict their correct position (including the variation) which is much more refined than filling in previous values, or using the average value. There may be used an adaptive schema to determine initial values for p and q by letting the subject breath in and out at their own pace, and determining the breathing pace via the ECG-output, for example with a piezo foil, or from the PPG. Hence the system is configured so that it can easily determine initial values for p and q. Typical values could be p=2, q=3, but as a starting value we can use values for p and q as the user 12 is currently using, and increase those numbers gradually.

In another embodiment the system 10 is operated so that it does not demand that the subject's breathings are exact in sync with the respiration, but it suffices to be almost in sync. From the theory of weakly coupled chaotic systems it is known that if $|n \phi_H - m \phi_R| < \epsilon$, where n and m are integers, $\phi_H$ and $\phi_R$ are the phases of the heart and respiratory signals respectively, and $\epsilon$ is a sufficiently small constant number the signals can be considered as being phase locked.

The system 10 described above with reference to FIGS. 1 to 4 includes means for making the system 10 more flexible and for optimizing the coherence of the subject 12. The current system 10 is based upon the premise that whilst it is very efficient to use simple paced breathing (or alternatively the VCRS breathing guidance method) to induce a state of coherence, the experience of pleasure (or relaxation) cannot be maximized by rigorously sticking to such simple (or even VCRS based) breathing guidance. In particular the system 10 is designed so that once coherence is reached (using VCRS breathing guidance) and the subject 12 is starting to feel relaxed, then there is change to the operation of the system 10 (as controlled by the processor 16) that allows the subject 12 to breathe at a different (slower) rate than dictated originally by the system 10.

As relaxation of the subject 12 continues to increase, the subject 12 will reach a state where they no longer feel the need to be guided in their breathing, but would feel much more comfortable and relaxed by simply breathing at their own preferred rate, which may be achieved with the guidance being removed temporarily. From this state of free breathing, the system 10 is controlled so that a return to breathing guidance can be carried out in the situation where it is identified that the subject 12 has broken their coherent state, for example if they were disturbed by an interruption.

In the following, a system and method based upon simple breathing guidance is described to realize this preferred relaxation inducing breathing guidance system. Initially, the system 10 may start by choosing a breathing rate which many users 12 will experience as conducive to relaxation. In a preferred embodiment, the system 10 is operated to produce an optimal breathing rate of 0.085 hertz, so the system 10 will select p (while q=p) in an initial phase such that this rate of 0.085 hertz is reached.

During the initial phase, the subject 12 will be in coherence almost immediately, but not necessarily with the optimal degree of comfort, pleasure or relaxation (as described above). During the initial phase the respiratory sinus arrhythmia (RSA) of the subject 12 is measured and small perturbations of the breathing rate of 0.085 hertz are introduced using well known optimization techniques (for example incremental increase or decrease of the rate) such that the RSA is optimal. The subject 12 may get feedback of this operation, or may even be encouraged to direct the increase or decrease of the rate manually. After a short while the subject 12 will have reached an optimal RSA.

While the RSA will be optimal after some time, for the reasons outlined above, the subject 12 may want to deviate from the paced optimal rate, and will start breathing at their own preferred rate. A further reason to desire to breathe at their own rate may be if the physical activity will change, for example during sports, staircase climbing etc. The system 10 can detect the deviation and may stop the pacing commands, or modify the pacing commands that the user 12 gets feedback on the deviation, for example by commands slower or faster, or by stopping the commands totally. Providing the user continues to maintain coherence (as measured by the system), the system does not need to re-introduce the paced breathing.

Optionally, as soon as the system 10 detects that the subject 12 is again breathing at a constant rate during their free breathing, the system 12 may propose (by giving a signal or other indication) that it may be enjoyable for the user 12 to pursue paced breathing, for example by decreasing the pacing rate to that which the user 12 has adopted during their voluntary breathing period. The automatic pacing system may then start again as introduced in the initial phase above.

If the system 10 detects that the subject 12 is losing coherence for any reason the system 10 may be programmed to either propose (by giving a signal or other indication) that it may be beneficial for the user 12 to restart paced breathing, or may alternatively enforce paced breathing. The automatic pacing system may then start again as introduced in the initial phase above, for example at the pacing rate which the user 12 has adopted during the voluntary breathing period when they were still in a coherent state.

In a further embodiment of the system 10 described above, it is proposed to replace the simple breathing guidance system with a system which uses VCRS based breathing guidance in at least one of the phases. Preferably, VCRS is used in the initial phase (instead of the proposed 0.085 Hz of the simple system above). Optionally, VCRS may also be used for when the system again takes over from the free breathing period.

Figure 5:
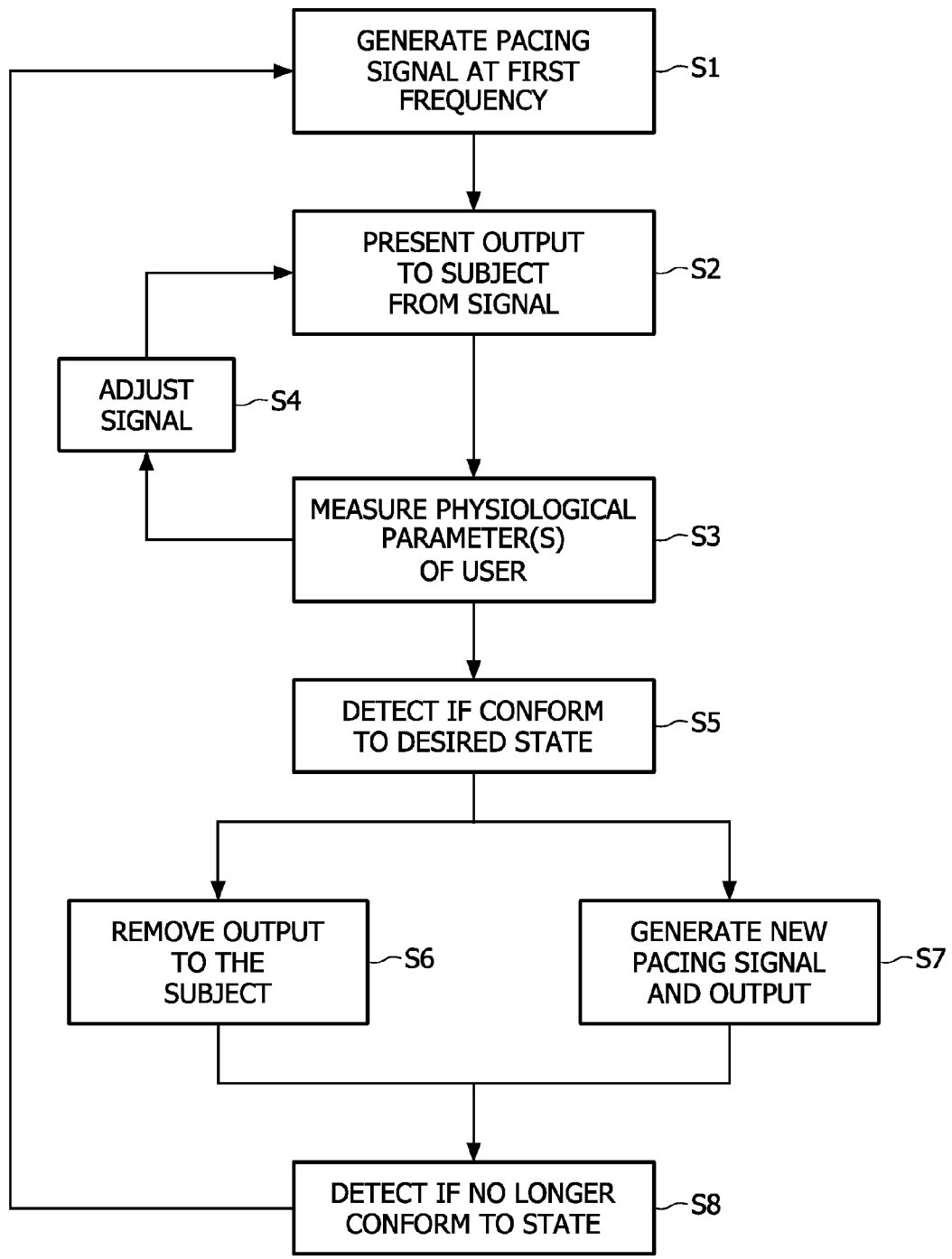
FIG. 5 is a flowchart of a method of operating the system of FIG. 1.

The methodology described above is summarised in FIG. 5. This Figure shows the steps in the preferred embodiment of the system of FIGS. 1 to 4. This method is for maintaining a state in the subject 12. The process comprises the first step, step S1, of generating the pacing signal 20 at the first frequency. This pacing signal 20 is to be used to control the breathing of the subject 12. At step S2, there is presented to the subject 12 an output based upon the generated pacing signal 20. This output can take a wide variety of different forms, but in a simple embodiment, will be some kind of visual display to the subject 12 to indicate the inhale and exhale of their breathing rate, as shown in FIG. 2.

The next step is step S3 of measuring one or more physiological parameters of the subject 12. The subject 12 is under observation, in an unobtrusive manner, to detect, for example, their current heart rate. Multiple parameters may be measured. These measurements, taken by the sensors 14, may be used as they are as the raw physical data (such as beats per minute or skin temperature), or may be converted to a value on a scale, such as an abstract "relaxation" scale. While the subject 12 is in this initial state, optionally, adjusting of the pacing signal according to feedback from the measured parameter(s) may take place, as indicated at step S4.

The processor 16 is constantly monitoring the output of the sensors 14, and this is reflected in the next step, step S5, of detecting that the measured parameter(s) conform to a desired state in the subject 12. The desired state of the subject can be defined in many different ways. For example, it can be defined with respect to the raw data read by the sensors 14, for example that a certain heart rate in beats per minute has been obtained. Equally the desired state may be achieved with reference to the abstract scale mentioned above. Multiple parameters may be used to determine whether the subject 12 is in the desired state, including data that has not been measured directly from the subject 12, such as the age of the subject, or the local room temperature or the time of day, etc.

Once the subject 12 has been detected to have entered the desired state, then either, at step S6, there is removal of the presentation to the subject 12 of the output based upon the generated pacing signal 20, or, at step S7, there is generation of a new pacing signal at a second frequency, and presenting to the subject of an output based upon the generated new pacing signal. The new pacing signal may be slower then the old pacing signal 20, and reflects the idea that once the subject 12 has entered the desired state, then they no longer need to be instructed to act in the manner that lead them to that desired state.

A final optional step is provided at step S8, wherein the method further comprises detecting that the measured parameter(s) no longer conform to the desired state in the subject 12, and thereby returning the subject 12 to the start of the process.

If the subject 12 is no longer detected to be in the desired state, then the system 10 can be configured so that the original pacing signal 20 is used again to derive an output to the subject 12, to help them return to the state. For example, the user may be startled by an interruption, which causes them to increase their heart-rate variability for example, and this could be perceived as removing them from the desired state. The process will restart at step S1.

The applying of feedback to the subject 12 may trigger any of the human senses for example by sound, scent, or a light which may change in colour or brightness. Some embodiments and applications are listed below.

If the feedback is given by means of headphones, the system 10 can modify for example by volume one headphone, say the left one, as an indication of inhale, and the other as exhale. It may done be using a voice with a relaxing intonation saying breath in and breath out.

Another feedback modality is transcutaneous electrical nerve stimulation (TENS) which might be modulated by the feedback controller.

If a subject is lying on bed, the system 10 can be used as a fall-in-sleep aid, the cardio signals are measured, by one of the methods described, but preferably with a ballistocardiogram, so that the subject 12 is free to move. The feedback can be given by modulating lights at a modest level, but also a relaxing humming sound at modest sound level which might be modulated by the feedback controller, or a (synthetic) music sound can be used.

During sports activities for example in the gym, or running or rowing, the sportsperson can get feedback, in particular runners often wear already a heart rate measurement device. In some activities a device is touched, such as the steering wheel of a bike, where easily the ECG can be measured, many other gym apparatuses have such contacts.

In hospitals patients are often already hooked up to SPO2-clips or EEG electrodes, so that the feedback controller can 'tap' these signals easily and send them to the feedback device. Similarly, in hospitals patients while being operated during partial anesthesia can breathe voluntarily. They are hooked up to SPO2-clips or EEG electrodes, so that the feedback controller can 'tap' these signals easily and send them to the feedback controller, and by applying VCRS the operation will be less stressful.

When driving a vehicle, the driver can be more relaxed if he is breathing in a VCRS way, in the vehicle chair there can be easily build in a heart rate detector, for example via an EMFi-film sensor based ballistocardiographic chair. If it appears that the driver relaxes too much and may fall asleep, the system 10 can operate such that the driver gets more aroused by increasing the breathing rate. Likewise, at the office working with a computer, the user 12 can be made more relaxed, see above.

If the user 12 gets mechanical ventilation, for example after surgery, the system 10 can dictate the ventilation pace of the ventilation machine such that it gets synchronized with the heart rate, in this case it is not voluntary respiration, but it is synchronized.

Instead of the two phase aid with feedback to inhale, and exhale, the system 10 can be extended to utilise multiple phases. Similar feedback techniques as mentioned above can be used, but the simplest embodiment is to use four (coloured) LED's pointing to a text, or just a variable text which phase is ongoing. This could use a particular form of yoga known as Nadi Shodhana Pranayama, or alternate nostril breathing encompasses four breathing phases: inhalation, internal retention (keeping lungs full), exhalation, and external retention (keeping lungs empty). The duration of breathing phases is controlled by mental counting in the ratio of 1:2:2:1, and in general p, q, r, and t, similar to the p and q discussed above, and shown in FIG. 4 can be used. Inhalation and exhalation take place through altering the active nostril, keeping the other nostril closed. Traditionally, the right nostril is closed by the thumb and left nostril is closed with the ring finger. For example, during the first cycle the subject 12 would inhale through the left nostril, keeping right nostril closed, than keep the breath in ("internal retention") with both nostrils closed, exhale through right nostril only, and finally close both nostrils during external retention. The next cycle starts by inhaling through the right nostril. The practice consists of ten cycles of slow breathing as described above.

It is also possible to use the system 10 to synchronize the heartbeats and the respiration with a locomotion frequency, for example the steps during walking or running, or the movements during rowing. The system 10 is intended to relax the subject in general, but include particular applications such as: decreasing the sleep-onset time, yoga exercises, lowering the blood pressure, relaxation during PC-use or television watching, vehicle driving, medicine, and sports. Furthermore, the present system 10 can be used to optimise the respiratory sinus arrhythmia (RSA) of the subject 12.

The invention claimed is:

1. A method of maintaining a state in a subject comprising:
in a single patient session:
   a) generating, by a processor, a pacing signal at a first frequency, to control the breathing of the subject, whereby said signal is received prior to receiving feedback from the subject as a measured physiological parameter,
   b) presenting to the subject, by an output device, an output based upon the generated pacing signal,
   c) measuring, by one or more sensors, at least two physiological parameters directly from the subject,
   d) detecting, by said processor, that the measured parameter(s) conform to a pre-determined range of values which place the subject in a desired state of coherency and relaxedness,
   e) introducing a time lapse to delay the removal of the pacing signal for a predetermined length of time after said detection has occurred at said step (d), and
   f) either removing, by the output device, the presentation to the subject of the output based upon the generated pacing signal after the predetermined length of time, or
   g) generating, by the processor, a new pacing signal at a second frequency, and presenting to the subject an output based upon the generated new pacing signal
   h) detecting, by the processor, that the measured parameter(s) no longer conform to a desired state in the subject at said second frequency,
   i) terminating, by the processor, the presentation of the second frequency to the subject, and
   j) re-introducing to the subject, by the output device, an output based upon the originally presented pacing signal generated at said first frequency at said step (a).

2. A method according to claim 1, and further comprising, prior to the detecting that the measured parameter(s) conform to a desired state in the subject, adjusting the pacing signal according to feedback from the measured parameter(s).

3. A method according to claim 1, and further comprising detecting that the measured parameter(s) no longer conform to a desired state in the subject, and presenting to the subject a warning indication.

4. A method according to claim 1, and further comprising, following detecting that the measured parameter(s) conform to a desired state in the subject, and prior to either removing the presentation to the subject of the output based upon the generated pacing signal, or generating a new pacing signal at a second frequency, and presenting to the subject (12) an output based upon the generated new pacing signal, maintaining the desired state in the subject for a predetermined length of time.

5. A system for maintaining a state in a subject comprising:
   a processor arranged to generate a pacing signal at a first frequency, to control the breathing of the subject, whereby said signal is received prior to receiving feedback from the subject as a measured physiological parameter,
   one or more output devices arranged to present to the subject an output based upon the generated pacing signal,
   one or more sensors arranged to:
      measure at least two physiological parameters directly from the subject,
   wherein the processor is further arranged to:
   adjust the pacing signal according to feedback from the at least two measured physiological parameter(s),
   detect that the measured parameter(s) conform to pre-determined range of values which place the subject in a desired state of coherency and relaxedness, and
   introduce a time lapse to delay the removal of the pacing signal for a predetermined length of time after said detection has occurred, and
either
   remove the presentation to the subject of the output based upon the generated pacing signal, or
   generate a new pacing signal at a second frequency, the output device(s) arranged to present to the subject an output based upon the generated new pacing signal,
   detect that the measured parameter(s) no longer conform to a desired state in the subject at said second frequency,
   terminate the presentation of the second frequency to the subject, and
   re-introduce to the subject an output based upon the original pacing signal generated at said first frequency.

6. A system according to claim 5, wherein the processor is further arranged, prior to detecting that the measured parameter(s) conform to a desired state in the subject, to adjust the pacing signal according to feedback from the measured parameter(s).

7. A system according to claim 5, wherein the processor is further arranged to detect that the measured parameter(s) no longer conform to a desired state in the subject, and the output device(s) is arranged to present to the subject a warning indication.

8. A system according to claim 5, wherein the processor is further arranged, following detecting that the measured parameter(s) conform to a desired state in the subject, and prior to either removing the presentation to the subject of the output based upon the generated pacing signal, or generating a new pacing signal at a second frequency, and presenting to the subject an output based upon the generated new pacing signal, to maintain the desired state in the subject for a predetermined length of time.

* * * * *